United States Patent [19]

Youssefyeh et al.

[11] Patent Number: 4,820,729

[45] Date of Patent: Apr. 11, 1989

[54] N-SUBSTITUTED-AMIDO-AMINO ACIDS

[75] Inventors: Raymond D. Youssefyeh, Tarrytown; Jerry W. Skiles, Tuckahoe, both of N.Y.; John T. Suh, Greenwich, Conn.; Howard Jones, Ossining, N.Y.

[73] Assignee: Rorer Pharmaceutical Corporation, Fort Washington, Pa.

[21] Appl. No.: 248,172

[22] Filed: Mar. 30, 1981

[51] Int. Cl.[4] .............. A61K 31/215; A61K 31/195; C07C 101/02; C07C 101/72; C07C 61/08

[52] U.S. Cl. .................................. 514/542; 514/563; 560/38; 562/455; 562/507

[58] Field of Search .............. 260/112.5 R; 514/542, 514/563; 560/38; 562/455, 507

[56] References Cited

U.S. PATENT DOCUMENTS

| | | | |
|---|---|---|---|
| 2,799,670 | 7/1957 | Laufer et al. | 260/112.5 R |
| 3,607,859 | 9/1971 | Feder | 260/112.5 R |
| 3,799,918 | 3/1974 | Mazur | 260/112.5 R |
| 4,076,705 | 2/1978 | Hirai et al. | 260/112.5 R |
| 4,086,136 | 4/1978 | Isowa et al. | 260/112.5 R |
| 4,116,768 | 9/1978 | Isowa et al. | 260/112.5 R |
| 4,165,311 | 8/1979 | Isowa et al. | 260/112.5 R |
| 4,176,116 | 11/1979 | Hassall et al. | 260/112.5 R |
| 4,183,910 | 1/1980 | Levine | 260/112.5 R |
| 4,187,216 | 2/1980 | Hassall et al. | 260/112.5 R |
| 4,238,392 | 12/1980 | Vinick | 260/112.5 R |
| 4,256,761 | 3/1981 | Suh et al. | 260/112.5 R |

FOREIGN PATENT DOCUMENTS 0012401 6/1980 European Pat. Off. ...... 260/112.5 R

OTHER PUBLICATIONS

G. R. Pettit, Synthetic Peptides 5, (1980) 134, 135, 164.
G. R. Pettit, Synthetic Peptides 4, 165 (1976) 150, 151.

Primary Examiner—Delbert R. Phillips
Attorney, Agent, or Firm—Scully, Scott, Murphy & Presser

[57] ABSTRACT

Compounds of the formula

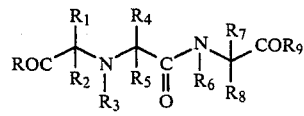

wherein

R and $R_9$ are independently hydroxy or lower alkoxy, $R_1$ and $R_2$ are hydrogen or lower alkyl, aryl-lower alkyl having from 7 to 12 carbon atoms, or heterocyclic-lower alkyl having from 6 to 12 carbon atoms, $R_3$, $R_4$, $R_5$, $R_7$ and $R_8$ are hygrogen or lower alkyl, $R_6$ is cycloalkly having from 3 to 20 carbon atoms, aryl or aryl-lower alkyl, and the aryl group contains from 6 to 10 carbon atoms, and their pharmaceutically acceptable, nontoxic acid addition salts and where R or $R_9$ or both are hydroxy, their pharmaceutically acceptable, nontoxic basic salts possess antihypertensive activity.

20 Claims, No Drawings

N-SUBSTITUTED-AMIDO-AMINO ACIDS

This invention relates to new chemical compounds having valuable pharmaceutical activity. It particularly relates to compounds possessing hypertensive and angiotensin converting enzyme inhibitory activity and having the structure

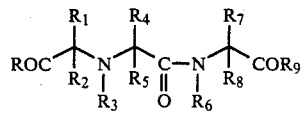

wherein
- R and $R_9$ are independently hydroxy, lower alkoxy, lower alkenoxy, di(lower alkyl)amino-lower alkoxy, hydroxy-lower alkoxy, acylamino-lower alkoxy, acyloxy-lower alkoxy, aryloxy, aryloxyl-lower alkoxy, amino, lower alkylamino, di-lower alkylamino, hydroxyamino, or aryl-lower alkylamino,
- $R_1$, $R_2$, $R_3$, $R_4$, $R_5$, $R_7$ and $R_8$ are independently hydrogen, alkyl having from 1 to 20 carbon atoms, alkenyl having from 2 to 20 carbon atoms, or alkynyl having from 20 to 20 carbon atoms, aryl-lower alkyl having from 7 to 12 carbon atoms or heterocyclic-lower alkyl having from 6 to 12 carbon atoms,
- $R_2$ and $R_3$ taken together with the carbon and nitrogen to which they are respectively attached and $R_3$ and $R_5$ taken together with the nitrogen and carbon to which they are respectively attached may form an N-heterocycle containing from 3 to 5 carbon atoms or 2 to 4 carbon atoms and a sulfur atom,
- $R_6$ is cycloalkyl, polycycloalkyl, partially saturated cycloalkyl and polycycloalkyl, cycloalkyl-lower alkyl, aryl, aryl-lower alkyl, aryl-lower alkenyl or, aryl-lower alkynyl, and their pharmaceutically acceptable, nontoxic acid addition salts, and when R or $R_9$ or both are hydroxy, their pharmaceutically acceptable nontoxic basic salts.

The alkyl groups per se or when present as substituents are preferably lower alkyl containing from 1 to 6 carbon atoms and may be straight chain or branched. These groups include methyl, ethyl, propyl, iso-propyl, butyl, isobutyl, amyl, hexyl and the like.

The alkenyl and alkynyl groups per se or when present as substituents preferably contain from 2 to 6 carbon atoms and may be straight chain or branched. These groups include vinyl, propenyl, allyl, isopropenyl, ethynyl and the like.

The alkyl, alkenyl, and alkynyl groups may carry substituents such as hydroxy, lower alkoxy, thio, lower alkylmercapto, amino, lower alkylamino, di(lower alkyl)amino, halogen, and nitro.

The aryl-lower alkyl and heterocyclic-lower alkyl groups include benzyl, phenethyl, naphthylmethyl, indolylethyl, indanylmethyl, indanylethyl and the like.

The cycloalkyl groups may be mono or polycyclic and contain from 3 to 20 carbons. These groups include cyclopropyl, cyclopentyl, cyclohexyl, cycloheptyl, bornyl, nor-bornyl, indanyl and the like. These groups may be partially unsaturated and carry substituents such as halogen, hydroxy, lower alkyl, lower alkoxy, amino lower alkylamino, di(lower alkyl)amino, thiol, lower alkylmercapto, nitro, and trifluoromethyl.

The aryl groups contain from 6 to 10 carbon atoms and include such groups as phenyl and α- or β-naphthyl and fused phenyl-cycloalkyl such as indanyl.

The aryl and aralkyl groups may carry one or more substituents such as lower alkyl, lower alkenyl, lower alkynyl, hydroxy, lower alkoxy, amino, lower alkylamino, di(lower alkyl)amino, thiol, lower alkylmercapto, hydroxy-lower alkyl, amino-lower alkyl, thio-lower alkyl, nitro, halogen, trifluoromethyl, methylenedioxy, ureido, or guanidino.

The acyl groups are preferably lower alkanoyl containing from 1 to 6 carbon atoms and benzoyl.

The halogen group may be fluorine, chlorine, bromine and iodine.

Suitable acid addition salts may be formed from inorganic acids such as hydrochloric, sulfuric and phosphoric, and organic acids such as acetic, lactic, citric, malic, maleic, fumaric, succinic, benzoic, hydroxybenzoic, aminobenzoic, nicotinic and the like.

Suitable basic salts may include the salts of alkali and alkali earth metals such as sodium, lithium, potassium, magnesium and calcium, as well as iron and salts of ammonia, amines, and quaternaries.

The compounds of the present invention may contain one (1) or more asymmetric carbon atoms and may exist in racemic and optically active forms. All of these forms are contemplated to be within the scope of the present invention.

The compounds of the present invention are prepared by the reaction of a compound of the formula $$R_6\text{-}NH_2$$

with a compound of the formula

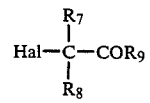

to give a compound of the formula

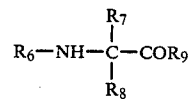

which is then reacted with an ester of the formula

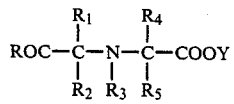

to give the desired compound.

As an alternative approach, a dipeptide of the structure

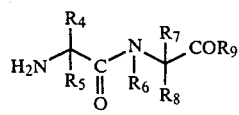

is reacted with an α-keto-acid or ester of the structure

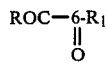

and the imine is reduced to give a compound of the structure

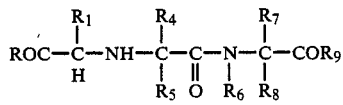

In the above sequence of reactions, $R$-$R_9$ are the same as described above, Hal is halogen and Y is lower alkyl.

Preferably, R and $R_9$ are hydrogen or lower alkyl, $R_2$, $R_5$, $R_7$ and $R_8$ are hydrogen, $R_1$ and $R_4$ are lower alkyl, $R_3$ is hydrogen, and $R_6$ is cycloalkyl, aryl, and aralkyl.

The invention will be more fully illustrated from the examples which follow. These examples are given by way of illustration and are not to be considered as limiting. A method of reducing the blood pressure in hypertensive animals comprises the administration of an antihypertensively effective amount of a compound of the invention.

EXAMPLE 1

A. Tert-Butyl N-(exo-Norbornyl) Glycinate

Exo-aminonorborane (50 g, 0.451 mol) was dissolved in ethanol (800 ml) and then triethylamine (55 g, 0.545 mol) was added. To this solution was added dropwise tert-butyl-bromacetate (87 g, 0.446 mol) which was dissolved in ethanol (50 ml). The resulting mixture was stirred overnight at room temperature. Ethanol was evaporated and water was added to the residue. The product was extracted twice into chloroform. The combined chloroform extract was washed twice with water, dried over magnesium sulfate, filtered, and evaporated to give the product as a pale yellow oil (78 g, 78%).

B. Tert-Butyl N-Carbobenzyloxy (L-Alanyl)-N-(exo-Norbornyl) Glycinate

Tert-butyl N-(exo-norbornyl) glycinate (22.4 g, 0.1 mol) and N-carbobenzyloxy-L-alanine (22.3 g, 0.1 mol) were dissolved in methylene chloride (300 ml) and the solution was chilled in an ice bath. To this solution was added dicyclohexylcarbodiimide (20.6 g, 0.1 mol). The reaction mixture was stirred for 15 minutes with external cooling and then for an hour and a half at room temperature. Precipitated dicyclohexylurea was filtered and washed with ether. The filtrate was evaporated to give initially a colorless oil which crystallized from n-hexane/ether to afford a colorless solid (33.4 g, 77.7%); m.p. 93°–95°; $[\alpha]_D^{CHCl_3} = +3.07°$. From the filtrate was obtained a second crop as a pale yellow oil which crystallized slowly (8 g).

C. N-Carbobenzyloxy (L-Alanyl)-N-(exo-Norbornyl) Glycine

Tert-butyl N-carbobenzyloxy (L-alanyl)-N-(exo-norbornyl) glycinate (20 g, 0.0465 mol) was added to cool trifluoroacetic acid (125 ml). The reaction mixture was stirred for 15 minutes with external cooling (ice bath) and then for two and a half hours at room temperature. Trifluoroacetic acid was distilled at 30° under vacuum. The residue was dissolved in chloroform, washed twice with water, dried over magnesium sulfate, filtered and evaporated to give the desired product (10.9 g, 60%) as a pale yellow foam; m.p. 52°, $[\alpha]_D^{CHCl_3} = -1.62°$.

EXAMPLE 2

A. Tert-Butyl N-Carbobenzyloxy(L-Phenylalanyl)-N-(Exo-Norbornyl)Glycinate

Tert-butyl N-(exo-norbornyl) glycinate (18.8 g, 0.0836 mol) and N-carbobenzyloxy-L-phenylalanine (25 g, 0.0836 mol) were dissolved in methylene chloride (600 ml). To the resulting solution was added dicyclohexylcarbodiimide (19.0 g, 0.0922 mol). The reaction was stirred at room temperature for four hours. Precipitated dicyclohexylurea was filtered and washed with a small amount of ether. The filtrate was concentrated and ether was added to the residue in order to precipitate more dicyclohexylurea. The dicyclohexylurea was filtered and the filtrate was evaporated to afford the product as a pale yellow oil (49.7 g).

B. N-Carbobenzyloxy(L-Phenylalanyl)-N-(exo-Norbornyl)-Glycine

To tert-butyl N-carbobenzyloxy (L-phenylalanyl)-N-(exonorbornyl) glycinate (9.5 g, 0.0188 mol) was added trifluoroacetic acid (75 ml). The resulting solution was stirred for 15 minutes with external cooling (ice bath) and then for an hour and a half at room temperature. Trifluoroacetic acid was evaporated at 30° under vacuum. The residue was dissolved in chloroform and washed twice with water. The organic layer dried over magnesium sulfate, filtered, and evaporated to afford a pale yellow gum. The product crystallized from n-hexane/ether to afford a colorless solid (6.0 g, 71%), M.P. 63.5°.

C. L-Phenylalanyl-N-(exo-Norbornyl) Glycine

N-Carbobenzyloxy (L-phenylalanyl)-N-(exo-norbornyl) glycine (2.5 g, 5.56 mmols) was added to a saturated solution of HBr in glacial acetic acid (20 ml) which had been chilled in an ice bath. The resulting solution was stored for fifteen minutes with external cooling and then for an hour at room temperature. Most of the acetic acid was evaporated and ether was added to the residue to yield the hydrobromide as a yellow solid which was filtered and washed with ether. The salt was redissolved in chloroform and stirred with charcoal. The charcoal was filtered and the filtrate was evaporated. The product was crystallized from ether to give pale yellow crystals (1.7 g, 75%).

EXAMPLE 3

A. Tert-Butyl N-(Cyclopentyl)-Glycinate

Cyclopentyl amine (50.0 g, 587 mmols) was dissolved in anhydrous ether (500 ml) and triethylamine (69.3 g, 685 mols) was added. The resulting solution was cooled in an ice bath and then tert-butyl bromoacetate (95.4 g, 489 mmols) in ether (150 ml) was added slowly over approximately three hours. The reaction mixture was allowed to stir overnight at room temperature. The reaction was acidified to pH 1 with aqueous hydrochloric acid and the layers were separated. The aqueous layer was washed with ethyl acetate and then basified to pH 10 with aqueous ammonium hydroxide. The product was extracted several times into methylene chloride and the combined organic extract was washed twice with water, once with brine, dried over magnesium sulfate, filtered, and evaporated to yield the desired product as a slightly yellow oil (56.9 g, 58.4%).

B. Tert-butyl N-Carbobenzyloxy (L-Alanyl)-N-(Cyclopentyl)Glycinate

Tert-Butyl N-(cyclopentyl) glycine (16.3 g, 81.8 mmols) was dissolved in methylene chloride (500 ml). The reaction mixture was cooled in an ice bath and then dicyclohexylcarbodiimide (16.9 g, 81.8 mmols) dissolved in a small amount of methylene chloride was added. N-carbobenzyloxy-L-alanine (18.3 g, 81.8 mmols) in methylene chloride (50 ml) was added dropwise over thirty minutes with external cooling. The reaction mixture was stirred overnight at room temperature. Precipitated dicyclohexylurea was filtered and washed with a small amount of methylene chloride. The filtrate was evaporated and the residue was dissolved in ether and allowed to stand to precipitate more dicyclohexylurea which was filtered. The filtrate was evaporated and to the residue was added n-hexane. Upon scratching and cooling colorless crystals of the desired product (30 g, 91%) formed; m.p. 73°–74°, $[\alpha]_D^{21}$ (EtOH)= −23.044°.

C. N-Carbobenzyloxy(L-Alanyl)-N-(Cyclopentyl)-Glycine

Tert-Butyl N-carbobenzyloxy (L-alanyl)-N-(cyclopentyl) glycinate (19.9 g, 49.2 mmols) was dissolved in anisole (50 g, 492 mmols) and then trifluoroacetic acid (111 g, 974 mmols) was added. The reaction mixture was stirred for three hours at room temperature. Trifluoroacetic acid was evaporated at 30° under vacuum. The residue was dissolved in ether and washed four times with water. The acidic product was extracted several times into aqueous potassium carbonate and the layers were separated. The combined aqueous extracts were washed twice with ether and then acidified cautiously to pH 1 by the dropwise addition of concentrated hydrochloric acid. The precipitated product was extracted several times into ether. The ether was washed with water, dried over magnesium sulfate, filtered and evaporated. The residue was redissolved in ether and allowed to stir with charcoal for thirty minutes. The charcoal was filtered and the filtrate was evaporated to afford the crude product (16.0 g). The crude product was separated by HPLC using acetic acid/ethyl acetate/n-hexane (2:49:49) as eluant. The pure product was obtained as a colorless solid (9.9 g, 52.6%); m.p. 48°–54°; $[\alpha]_D^{21}$ (EtOH)= −20.644°.

D. L-Alanyl-N-(Cyclopentyl)-Glycine

N-Carbobenzyloxy-(L-alanyl)-N-(cyclopentyl) glycine (8.7 g, 25.0 mmol) was dissolved in methanol (200 ml) and 10% Pd/c (1 g) was added. The resulting mixture was hydrogenated at an initial pressure of 50 psi. overnight. The reaction mixture was filtered through Celite, the filter cake was washed with methanol and the filtrate was evaporated to dryness to afford a white solid. This material was portioned between water and ether. The aqueous layer was freeze-dried to yield the desired product as a colorless solid (2.7 g, 50.5%); 153°–156°; $[\alpha]_D^{21}$ (H$_2$O)= +11.677°.

E. N-(1-Carbethoxyehtyl)-L-Alanyl-N'-Cyclopentyl Glycine Meleate

A mixture of 4.39 g (0.01 m) of CBZ-L-alanyl-N-cyclopentyl glycine benzyl ester, 3.5 g (0.03 m) ethyl pyruvate, 300 mg 10% palladium on charcoal in 50 ml ethanol was hydrogenated until uptake of hydrogen ceased.

It was filtered, 1.16 g (0.01 m) of maleic acid was added and evaporated to dryness. The crude oil was washed with ethyl acetate and crystallized from ethanol-ether.

EXAMPLE 4

A. Ethyl N-Carbobenzylloxy-L-Isoleucyl-N-(Exo-Norbornyl) Glycinate

Ethyl N-(exo-norbornyl) glycinate (7.8 g, 39.5 mmols) and N-carbobenzyloxy-L-isoleucine (10 g, 39.5 mmols) were dissolved in methylene chloride (250 ml). To the resulting solution was added dicyclohexylcarbodiimide (8.3 g, 40.3 mmols). The reaction was stirred for two and a half hours at room temperature. Precipitated dicyclohexylurea was filtered and washed with ether. The filtrate was concentrated and ether was added to the residue in order to precipitate a second portion of dicyclohexylurea which was filtered. The filtrate was evaporated to yield the desired product as a pale yellow viscous oil (16.8 g, 96%).

EXAMPLE 5

A. Ethyl N-(5-Indanyl)-Glycinate

To a solution of 5-aminoindan (15.0 g, 0.1128 mol) and triethylamine (11.92 g, 0.1184 mol) in 200 ml ethanol was added dropwise ethyl bromoacetate (18.83 g, 0.1128 mol). After the addition was complete the mixture was stirred at room temperature for 24 h and concentrated in vacuo. The residue was dissolved in ether, washed with H$_2$O (4×300 ml), brine and dried (MgSO$_4$). Concentration of the volatiles in vacuo provided a crystalline material which was recrystallized from petroleum ether; b.p. 30°–60° C., m.p. 49° C.

B. Ethyl N-Carbobenzoxy-L-Alanyl-N-(5-Indanyl)-Glycinate

To a solution of ethyl N-(5-indanyl)-glycinate (10.6 g, 48.4 mmol) and N,N'-dicyclohexylcarbodiimide (10.5 g, 50.8 mmol) in 200 ml CH$_2$Cl$_2$ at 0° C. was added dropwise a solution of N-carbobenzyloxy-L-alanine (11.3 g, 50.8 mmol) in 100 ml CH$_2$Cl$_2$. After the addition was completed the solution was stirred 10 min., warmed to room temperature and stirred overnight. The solution was filtered and concentrated in vacuo. The residue was dissolved in ether, filtered, washed with saturated NaHCO$_3$, 10% aqueous HCl (5x), brine and dried MgSO$_4$). Concentration of the volatiles in vacuo provided the product.

C. N-Carbobenzoxy-L-Alanyl-N-(5-Indanyl)-Glycine

To a solution of ethyl N-carbobenzoxy-L-alanyl-N-(5-indanyl)-glycinate (14.0 g, 33.0 mmol) in 150 ml ethanol was added sodium hydroxide (25 ml of a 2N aqueous solution, 49.5 mmol) and mixture stirred at room temperature for 20 h. The volatiles were removed under reduced pressure and the residue dissolved in ether and saturated sodium bicarbonate. The organic layer was separated and extracted with saturated sodium bicarbonate. The combined basic extracts were cooled in an ice bath and acidified with concentrated HCl. The aqueous solution was extracted thoroughly with CH$_2$Cl$_2$. The combined organic extracts were dried (MgSO$_4$) and concentrated in vacuo.

D. L-Alanyl-N-(5-Indanyl)-Glycine

A solution of N-carbobenzoxy-L-alanyl-N-(5-indanyl)glycine (4.5 g) and 10% palladium on carbon (1.0 g) in 250 ml ethanol was hydrogenated at 25 psi for 2 h and filtered. Concentration of the volatiles in vacuo provided a residue which was dissolved in H$_2$O and filtered over Celite. Lyophilization of the filtrate provided the crystalline (m.p. 119°–120° C.) product.

E. N-(1-Carboxyethyl)-L-Alanyl-N-(5-Indanyl)-Glycine Pyruvate

To a solution of N-carbobenzoxy-L-alanyl-N-(5-indanyl)glycine (3.8 g, 9.59 mmol) and pyruvic acid (4.2 g, 47.9 mmol) in 200 ml ethanol was added 10% palladium on carbon (9.5 g). The mixture was hydrogenated at 50 psi for 4 h, filtered and concentrated in vacuo. The residue was dissolved in H$_2$O and ethyl acetate. The aqueous layer was washed twice with ethyl acetate, once with ether, and lyophilized to provide the crystalline (m.p. 140° C. dec.) product.

EXAMPLE 6

A. N'-(Carbobenzyloxy)-Alanyl-N-(p-Tolyl)-Glycine t-Butyl Ester

P-Tolyl-glycine t-butyl ester (20 g, 0.0954 mol) was taken up in a 3-necked round bottom flask (IL) equipped with a dropping funnel, condenser (drying tube), thermometer and a stirring bar. The ester was dissolved in 250 ml methylene chloride, and to this was added a solution of N,N-dicyclohexylcarbodiimide (27 g, 0.1311 mol) in methylene chloride (100 ml). The temperature of the reaction mixture was brought to 0° C. (ice bath). Carbobenzyloxy-L-alanine (33.5 g, 0.15 mol) in methylene chloride was added dropwise (1.5 h). On completion of the addition the reaction mixture was allowed to warm to room temperature and stirred overnight. The reaction mixture was again cooled down to 0° C. to completely precipitate the DCC urea, filtered and the filtrate was concentrated on rotary evaporator to give a crude yellow thick liquid. The crude product was dissolved in diethyl ether (anhydrous, 400 ml) and extracted 3x with IN HCl and 3x with sodium bicarbonate (saturated). The ether solution was dried on magnesium sulfate (anhydrous) and the ether was evaporated to give a very thick yellow liquid.

B. N'-(Carbobenzyloxy)-Alanyl-N-(p-Tolyl)-Glycine

To a solution of 9.5 g N'-(carbobenzyloxy)-alanyl-N-(p-tolyl)-glycine t-butyl ester in methylene chloride (16 ml) was added dropwise 10 ml of TFA at 0° C. On completion of TFA addition the temperature of the reaction mixture was allowed to come up to room temperature and the mixture was stirred for 54 h. At the end of the reaction methylene chloride was evaporated in vacuo and the residue was dissolved in carbon tetrachloride (100 ml). This solution was washed 3x with distilled water (50 ml portions) and carbon tetrachloride was evaporated. The resulting residue was dissolved in diethyl ether (150 ml) and extracted 3x with sodium bicarbonate (saturated). The combined sodium bicarbonate layers were acidifed with 10% hydrochloric acid to pH 4–5 and extracted with diethyl ether. Ether was evaporated in vacuo to give the pure acid. TLC (methanol-ethyl acetate, 2:3) gave one spot. NMR spectrum was consistent with the assigned structure.

C. Alanyl-N-(p-Tolyl)-Glycine Hydrobromide

N'-(Carbobenzyloxy)-alanyl-N-(p-tolyl)-glycine (1.7 g, 0.0046 mol) was dissolved in acetic acid (glacial, 5 ml) and the solution was cooled to 0° C. (ice bath). To this solution was added a saturated solution of hydrogen bromide in acetic acid (glacial, 4.6 ml). The reaction mixture was allowed to warm to room temperature and stirred for an additional half hour. The reaction mixture was diluted with 150 ml of ether to give a semisolid hydromide salt. The salt was dissolved in distilled water (100 ml) and was washed 3x with 50 ml portions of ether. The water soluble salt gave a single spot on TLC (methanol) and also n-butanol-acetic acid-water. The solid salt was obtained after evaporating the water on a freeze drier. The hydrobromide was hygroscopic, mp 83°–87° C.

D. N'-(1-Carboethoxyethyl)-Alanyl-N-(p-Tolyl)-Glycine T-Butyl Ester

In a dry hydrogenation bottle N'-(carbobenzyloxy)alanyl-N-(p-toyl)glycine t-butyl ester (25 g, 0.0590 mol) was dissolved in ethanol (absolute, 60 ml). To this was added acetic acid (glacial, 30 ml), ethyl pyruvate (13 g, 0.1126 mol) and 10% palladium/charcoal (4.5 g). An overnight hydrogenation of this mixture used 12 psi. The reaction mixture was worked up by adding 5 g of Celite and filtering the palladium/charcoal. Ethanol and acetic acid were removed in vacuo. The crude product examined on TLC (ethyl acetate) was found to contain two diastereomers of the required product. The diastereomers can be separated by HPLC (hexane-ethyl acetate). A mixture of diastereomers of the separated isomers were characterized by NMR and mass spectroscopy.

E. N'-(1-Carboethoxyethyl)-Alanyl-N-(p-Tolyl)-Glycine and Its Calcium Salt

To a solution of N'-(1-carboethoxyethyl)-alanyl-N-(p-tolyl)-glycine t-butyl ester (2.6 g, 0.0066 mol) in methylene chloride (26 ml) was added dropwise trifluoroacetic acid (14.4 ml, 0.19 mol) at 0° C. (ice bath). The temperature was allowed to go to room temperature and the reaction mixture was stirred for 72 h. At the end of the reaction methylene chloride and trifluoroacetic acid were evaporated in vacuo. The crude product thus obtained was purified by chromatography on IR-120 resin. The resin was washed with water and acidified with 6NCl. The compound was dissolved in 2 ml of distilled water and loaded onto the column. The column was washed with water and eluted with 5% ammonia to give 0.65 g of the desired compound. 0.57 g of the free acid was dissolved in water (25 ml) and reacted with calcium oxide (47.6 mg, 0.0009 mol). Any unreacted calcium oxide was removed by filtration and the resulting solution was freeze dried to give 0.61 g of the calcium salt, mp 165°–170° C.

EXAMPLE 7

A. Ethyl N-Carbobenzyloxy-L-Alanyl-N-Benzyl-Glycinate

To a solution of ethyl N-benzyl-glycinate (47.5 g, 0.268 mol) and N-carbobenzyloxy-L-alanine (60.0 g, 0.268 mol) in 600 ml of methylene chloride at 0° C. was added dropwise a solution of N,N'-dicyclohexylcarbodiimide (55.2 g, 0.268 mol) in 600 ml methylene chloride over a 1 hour period. After the addition was complete the solution was stirred for 10 min., warmed to room temperature and continued stirring overnight. The solution was filtered, washed with dilute aqueous HCl, H₂O, saturated NaHCO₃, brine, dried (MgSO₄). Concentration of the solution in vacuo yielded the oily product.

B. N-Carbobenzyloxy-L-Alanyl-N-Benzyl-Glycine

To ethyl N-carbobenzyloxy-L-alanyl-N-benzyl glycinate (11.2 g, 28.1 mmol) in 60 ml ethanol was added sodium hydroxide (2.2 g, 55.0 mmol). The mixture was stirred at room temperature for 18 hours. The solution was concentrated in vacuo and the remaining residue dissolved in water. The aqueous solution was washed with ether twice, cooled in an ice bath and acidified with concentrated HCl. The acidic solution was extracted thoroughly with ether. The combined organic extracts were dried (MgSO₄) and concentrated in vacuo to provide the carboxylic acid.

C. L-Alanyl-N-Benzyl-Glycine

A solution of N-carbobenzyloxy-L-alanyl-N-benzyl glycine (6.0 g) and 10% palladium on carbon (2.0 g) in 200 ml ethanol was hydrogenated at 50 psi for 4 hours and filtered. Concentration of the volatiles in vacuo provided a residue which was dissolved in H₂O and filtered. The aqueous solution was acidified with 25% aqueous HBr until pH 1 was obtained. The solution was lyophilized. The crystalline product was recrystallized from ether-acetonitrile (m.p. 84°–85° C.).

D. N-(1-Carboxyethyl)-L-Alanyl-N-Benzyl-Glycine Pyruvate

To a solution of N-carbobenzyloxy-L-alanyl-N-benzyl glycine (5.8 g, 15.6 mmol) and pyruvic acid (3.5 g, 39.1 mmol) in 200 ml absolute ethanol was added 10% palladium on carbon (0.5 g). The mixture was hydrogenated at 50 psi for 4 hours. The solution was filtered and concentrated in vacuo at room temperature. The residue was dissolved in H₂O and ethyl acetate. The aqueous layer was washed twice with ethyl acetate and once with ether and lyophilized to provide the crystalline product, m.p. 105°–108° C.

EXAMPLE 8

A. Ethyl N-(2-Indanyl) Glycinate

2-Aminoindan hydrochloride (50 g, 0.295 mol) was dissolved in acetonitrile (1 l) and triethylamine (65 g, 0.644 mol) was added. To the resulting solution was added dropwise ethyl bromoacetate (50 g, 0.297 mol) in acetonitrile (100 ml). The resulting mixture was stirred overnight at room temperature. Acetonitrile was evaporated and the residue was dissolved in chloroform. The chloroform was washed twice with water, dried over magnesium sulfate, filtered and evaporated to give the product as a tan oil (39.4 g, 62%) which was used in the next reaction without further purification. The product was characterized as its hydrochloride salt.

B. Ethyl N-Carbobenzyloxy (L-Alanyl)-N-(2-Indanyl) Glycinate

Ethyl N-(2-indanyl) glycinate (39.4 g, 0.180 mol) and Ncarbobenzyloxy-L-alanine (40 g, 0.179 mol) were dissolved in methylene chloride (600 ml) and the resulting solution was chilled in an ice bath. Dicyclohexylcarbodiimide (40 g, 0.190 mol) was added portionwise and the resulting mixture was stirred for 30 minutes with external cooling and then overnight at room temperature. Precipitated dicyclohexylurea was filtered and washed with a small amount of ether. The filtrate was evaporated to give the crude product as a dark oil which was chromatographed on silica-gel using ether as eluent to give the pure product as a tan gum (70.2 g, 92.4%).

C. N-Carbobenzyloxy-(L-Alanyl)-N-(2-Indanyl) Glycine

Ethyl N-carbobenzyloxy-(L-alanyl)-N-(2-indanyl) glycinate (40 g, 0.0991 mole) was added to a solution of potassium hydroxide (11.1 g, 0.198 mole) in ethanol (500 ml). The resulting mixture was stirred for three hours at room temperature. Ethanol was evaporated and the residue was dissolved in water. The aqueous solution was washed three times with ether. The aqueous solution was acidified to pH 2 with concentrated hydrochloric acid and the precipitated product was extracted several times into chloroform. The combined chloroform extract was washed with water, dried over magnesium sulfate, filtered and evaporated to give the product as a tan gum (25 g, 63.8%). The product was characterized as its dicyclohexylamine salt, m.p. 180°.

EXAMPLE 9

A. N'-(Carbobenzyloxy)-Isoleucyl-N-(p-Tolyl)-Glycine t-Butyl-Ester

The reaction was carried out in a similar manner as described in example 6A. p-Tolyl-glycine t-butyl ester (8.67 g, 0.0396 mol) was dissolved in methylene chloride (45 ml), mixed with a solution of N,N-dicyclohexylcarbodiimide (9.15 g, 0.0396 mol) in methylene chloride (30 ml) and reacted with a solution of carbobenzyloxy isoleucine (10 g, 0.0377 mol) in methylene chloride (60 ml).

B. N'-(Carbobenzyloxy)-Isoleucyl-N-(P-Tolyl) Glycine

N'-CBZ-isoleucyl-N-(p-tolyl)-glycine t-butyl ester (8 g) was dissolved in methylene chloride (13.5 ml) and reacted with TFA (8 ml) at 0° C. The reaction mixture was stirred at room temperature for 72 hours and worked up similarly as in example 7B. The pure acid isolated was a single spot on TLC (methanol-ethylacetate, 2:3) and had the expected NMR spectrum.

C. Isoleucyl-N-(P-Tolyl) Glycine

N'-CBZ-isoleucyl-N-(p-tolyl)-glycine (1 g, 0.00024 mol) was dissolved in acetic acid (glacial, 3.5 ml) and reacted with hydrogen bromide/acetic acid (2.5 ml). The reaction procedure is as described in example 6C. The product obtained after freeze-drying was characterized by TLC (methanol), NMR and mass spectroscopy.

EXAMPLE 10

N-(1-Carboxyethyl)-L-valyl-N-benzyl-glycine pyruvate

To a solution of N-carbobenzoxy-L-valyl-N-benzyl glycine (17.2 g, 44.6 mmol) and pyruvic acid (19.6 g, 0.223 mol) in 400 ml absolute ethanol was added 10% palladium on carbon (1.5 g). The mixture was hydrogenated at 50 psi for 4 hours. Filtration and concentration in vacuo provided an oily product which was purified as in example 7D.

EXAMPLE 11

N-(1-Carboxyethyl)-L-alanyl-N-(4-methylbenzyl)-glycine pyruvate

To a solution of N-carbobenzoxy-L-alanyl-N-(4-methylbenzyl)-glycine (5.8 g, 15.1 mmol) and pyruvic acid (3.3 g, 37.8 mmol) in 200 ml absolute ethanol was added 10 palladium on carbon (0.5 g). The mixture was hydrogenated at 30 psi for 4 hours and filtered. Concentration of the volatiles in vacuo provided an oil product which was purified as in example 7D.

By following the procedures in the above examples, the following additional compounds can be prepared:

N-[1-(S)-Ethoxycarbonyl-2-phenylethyl]alanyl-N-(1-indanyl)glycine
N-[1-(S)-Ethoxycarbonyl-3-methylbutyl]valyl-N-(p-bromophenyl)glycine
N-[1-(S)-Ethoxycarbonyl-3-phenylpropyl]isoleucyl-N-[(2-chloro-5-methoxy)phenyl]-glycine
N-[1-(S)-Ethoxycarbonyl-3-methylthiopropyl]alanyl-N-(3-cyanophenyl)glycine
N-[1-Ethoxycarbonyl-4-methylpentyl]alanyl-N-(3,4-dimethoxybenzyl)alanine
N-[1-(S)-Ethoxycarbonyl-3-phenylpropyl]alanyl-N-(3,5-dimethylphenyl)glycine
N-[1-(S)-Ethoxycarbonyl-2-(3-indolyl)ethyl]valyl-N-(m-tolyl)glycine
N-[1-(S)-Ethoxycarbonylethyl](p-chlorophenylalanyl)-N-(m-trifluoromethylphenyl)glycine
N-[1-Ethoxycarbonyl-3-methylbutyl]alanyl-N-(m-methoxyphenyl)glycine
N-[1-Ethoxycarbonylhexyl]phenylalanyl-N-(p-isopropylphenyl)glycine
N-(1,3-Dicarboxypropyl)isoleucyl-N-[(3,4-dimethoxyphenethyl)]glycine
N-[1-(S)-Ethoxycarbonyl-3-phenylpropyl]isoleucyl-N-[p-(n-butylphenyl)]-glycine
N-[1-(S)-Ethoxycarbonylethyl]methionyl-N-(4-t-butylphenyl)alanine
N-[1-(S)-carboxyethyl]valyl-N-(3-methylthiophenyl)alanine
N-[1-(S)-Carboxy-3-phenylpropyl]alanyl-N-(α-naphthyl)glycine
N-[1-(S)-Ethoxycarbonyl-2-phenylethyl]phenylalanyl-N-(2-chlorobenzyl)glycine
N-[1,3-Diethoxycarbonylpropyl]alanyl-N-(p-nitrophenyl)glycine
N-[1-(S)-Carboxy-3-methylbutyl]alanyl-N-(3,4-dihydroxyphenethyl)glycine
N-[1-(S)-Ethoxycarbonyl-3-phenylpropyl]alanyl-N-(o-carboxyphenyl)glycine
N-[1-(S)-Carboxy-2-phenylethyl]valyl-N-(m-biphenyl)glycine The compounds of the present invention have demonstrated potent activity (of the order of I$_{50}$ of 0.1 to 10.0 micromols) in inhibiting the angiotensin converting enzyme (ACEI activity) when tested by the method described in Science 196, 441-4 (1977). The compounds of the present invention have also demonstrated an I$_{50}$ of about 1 to 10 mg/kg P.O. in inhibiting infused angiotensin I in rats. As such, these would be very useful in the treatment of hypertension.

The compounds may be administered orally or parenterally in the treatment of hypertension, and it will be within the professional judgement and skill of the practioner to determine the amount to be administered. Suitable dosage forms include tablets, capsules, elixirs and injectables.

We claim:

1. Compounds of the formula

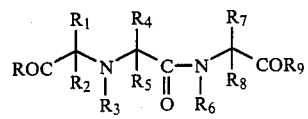

possessing angiotensin converting enzyme inhibitory activity, wherein

R and R$_9$ are independently hydroxy or lower alkoxy,
R$_1$ is hydrogen, lower alkyl or aryl-lower alkyl,
R$_2$, R$_3$, R$_4$, R$_5$, R$_7$ and R$_8$ are hydrogen or lower alkyl, and
R$_6$ is cycloalkyl having 3 to 20 carbon atoms, aryl-lower alkyl, or aryl, substituted and unsubstituted, and their pharmaceutically acceptable salts.

2. A compound of claim 1 wherein R$_6$ is cyclopropyl, cyclopentyl, cyclohexyl, cycloheptyl, bornyl, norbornyl, phenyl, benzyl, naphthyl or phenethyl, these groups may be substituted.

3. A compound of claim 1 wherein
R$_1$ is lower alkyl or aryl-lower alkyl,
R$_4$ is lower alkyl, and
R$_2$, R$_3$, R$_5$, R$_7$ and R$_8$ are hydrogen.

4. A compound of claim 3 wherein
R is lower alkoxy, and
R$_9$ is hydroxy.

5. A compound of claim 4 wherein R$_1$ is aryl-lower alkyl.

6. A compound of claim 4 wherein R is ethoxy and R$_1$ is phenethyl.

7. A compound of claim 1 wherein R$_4$ is methyl.

8. Compounds of the formula

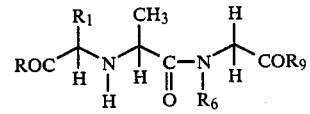

wherein
R and R$_9$ are independently hydroxy or lower alkoxy,
R$_1$ is aryl-lower alkyl or alkyl, and
R$_6$ is cycloalkyl having 3 to 20 carbon atoms, aryl-lower alkyl or aryl, substituted and unsubstituted; and their pharmaceutically acceptable salts.

9. A compound of claim 8 wherein
R$_6$ is cyclopropyl, cyclopentyl, cyclohexyl, cycloheptyl, bornyl, norbornyl, phenyl, benzyl, naphthyl, or phenethyl, these groups may be substituted.

10. A compound of claim 8 wherein R$_6$ is benzyl, tolyl, or cycloalkyl of 3 to 10 carbon atoms.

11. A compound of claim 10 wherein $R_1$ is phenethyl,
R is ethoxy, and
$R_9$ is hydroxy.

12. A compound of the formula

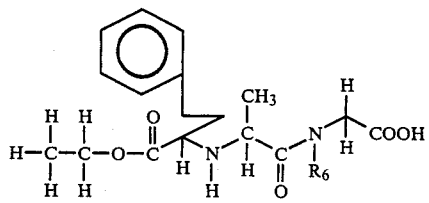

wherein
$R_6$ is cycloalkyl of $C_3$–$C_{10}$, aryl-lower alkyl or aryl, substituted and unsubstituted, and their pharmaceutically acceptable salts.

13. A compound of claim 12 wherein $R_6$ is cyclopropyl, cyclopentyl, cyclohexyl, cycloheptyl, bornyl, norbornyl, phenyl, benzyl, naphthyl, or phenethyl, these groups may be substituted.

14. A compound according to claim 12 wherein $R_6$ is benzyl.

15. A compound according to claim 12 wherein $R_6$ in p-tolyl.

16. A compound according to claim 12 wherein $R_6$ is cycloalkyl having from 3 to 10 carbon atoms.

17. A compound according to claim 3 wherein $R_6$ is cyclopentyl.

18. Compounds of the formula

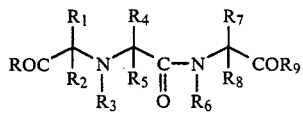

possessing angiotensin converting enzyme inhibitory activity, wherein
R and $R_9$ are independently hydroxy or lower alkoxy,
$R_1$ is hydrogen, lower alkyl, aryl-lower alkyl or aryl-lower alkoxy,
$R_2$, $R_3$ $R_4$, $R_5$ $R_7$ and $R_8$ are hydrogen or lower alkyl, and
$R_6$ is cycloalkyl having 3 to 20 carbon atoms and their pharmaceutically acceptable salts;

19. Compounds of the formula

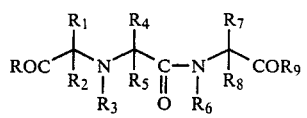

possessing angiotensin converting enzyme inhibitory activity, wherein
R and $R_9$ are independently hydroxy or lower alkoxy,
$R_1$ is hydrogen, lower alkyl or aryl-lower alkyl,
$R_2$, $R_3$, $R_4$, $R_5$, $R_7$ and $R_8$ are hydrogen or lower alkyl, and
$R_6$ is norbornyl;
and their pharmaceutically acceptable salts.

20. A method of reducing the blood pressure in hypertensive animals which comprises the administration of an anti-hypertensively effective amount of a compound according to claim 1.

* * * * *